Figure 1A:
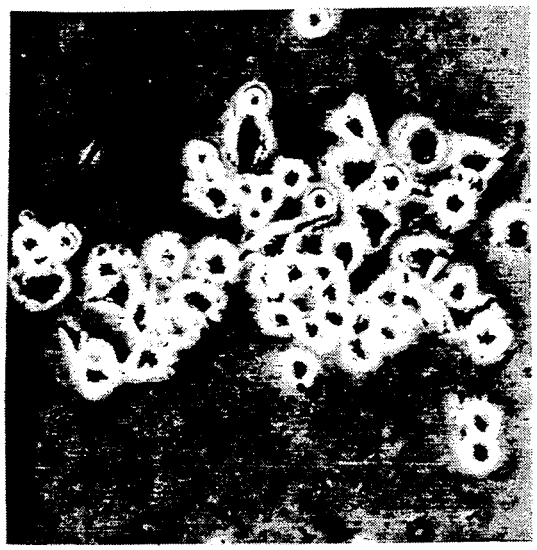

United States Patent [19]
Della Valle et al.

[11] Patent Number: 5,135,921
[45] Date of Patent: Aug. 4, 1992

[54] PHARMACEUTICAL COMPOSITIONS COMPRISING PHOSPHATIDYL CARNITINE FOR THE TREATMENT OF HUMAN PATHOLOGIES ASSOCIATED WITH NEURONAL DAMAGE

[75] Inventors: Francesco Della Valle, Padova; Aurelio Romeo, Rome, both of Italy

[73] Assignee: Fidia S.p.A., Padova, Italy

[21] Appl. No.: 518,528

[22] Filed: May 3, 1990

[30] Foreign Application Priority Data
May 3, 1989 [IT] Italy .................. 20358 A/89

[51] Int. Cl.$^5$ .................. A61K 31/685
[52] U.S. Cl. .................. 514/77; 514/78
[58] Field of Search .................. 514/78, 77

[56] References Cited

U.S. PATENT DOCUMENTS

| | | | |
|---|---|---|---|
| 4,343,816 | 8/1982 | Cavazza | 514/554 |
| 4,346,107 | 8/1982 | Cavazza et al. | 514/547 |
| 4,439,438 | 3/1984 | Cavazza | 514/357 |

FOREIGN PATENT DOCUMENTS 0348859  3/1990 · European Pat. Off.

OTHER PUBLICATIONS

Hintze, V et al. Lipids 10(1): 20–24 (1975).
Curti, D et al. Biological Psychiatry (1985).
Tempesta, JL Int. J. Clin. Pharm. Res. 3(4): 295–306 (1983).

Primary Examiner—Glennon H. Hollrah
Assistant Examiner—Gary E. Hollinden
Attorney, Agent, or Firm—Birch, Stewart, Kolasch & Birch

[57] ABSTRACT

We describe the use of phospholipidic carnitine derivatives of general formula

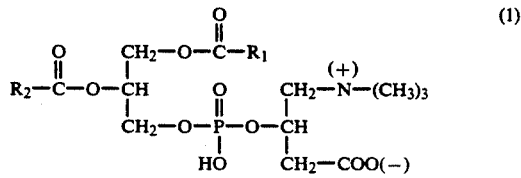

in their racemic or optically active form, wherein $R_1$ and $R_2$, equal or different, are radicals of linear or branched, saturated or monoor poly-unsaturated, aliphatic acids with 1 to 20 C for the preparation of pharmaceutical compositions having an activity as reproductive agent of the nerve fibers in the therapy of human pathologies associated with neuronal damages, more particularly in the therapy of peripheral neuropathies, of cerebrovascular diseases, of cerebral level traumas and of chronic neurodegenerative diseases.

10 Claims, 1 Drawing Sheet

PHARMACEUTICAL COMPOSITIONS COMPRISING PHOSPHATIDYL CARNITINE FOR THE TREATMENT OF HUMAN PATHOLOGIES ASSOCIATED WITH NEURONAL DAMAGE

DESCRIPTION

The present invention refers to the use of derivatives of phosphatidyl carnitine and of their pharmaceutically acceptable salts, having the formula:

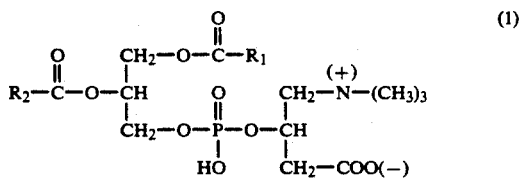

in their racemic or optically active form, wherein $R_1$ and $R_2$, equal or different, are radicals of aliphatic acids of from 1 to 20 C atoms, with linear or branched chains, saturated or mono- or polyunsaturated, preferably radicals of pivalic-, lauric-, myristic-, palmitic-, palmitoleic-, stearic-, oleic-, linoleic-, linolenic-, or arachidonic-acid for the preparation of pharmaceutical compositions active as reproductive agents of the nerve fibers in the therapy of human diseases associated with neuronal damages, particularly in the therapy of peripheral neuropathies, cerebrovascular diseases, cerebral level traumas and chronic neurodegenerative diseases. For the sake of clarity and simplicity, in the present text the carnitine phosphatidyl derivatives, the use of which is an object of the present invention, having the formula (I), will be generically referred to as phosphatidyl carnitine.

Phosphatidyl carnitine is a known substance; its method of preparation and physico-chemical properties were described by H. Hintze & G. Gercken in Lipids vol. 10, n.1 (1975) p. 20–24; for this substance, however, no possible therapeutical uses were mentioned.

We now have surprisingly found that phosphatidyl carnitine is active as reproductive agents of the nerve fibers in the therapy of human diseases connected with neuronal damages, particularly in the therapy of peripheral neuropathies, of cerebrovascular diseases, of cerebral level traumas and of chronic neurodegenerative diseases. More particularly, examples of human diseases associated with neuronal damages, both morphologic and functional, are the following:

a. Damage of traumatic, metabolic or toxic origin of the peripheral nervous system (peripheral neuropathies).

b. Damage of traumatic or vascular origin of the cerebral nervous system (neurovascular diseases and traumas at cerebral level).

c. Damage associated with aging of the central nervous system.

d. Damage due to still unknown etiopathologic causes (chronic neurodegenerative diseases) or infectious or tumoral diseases. As peripheral neuropathies we intend a group of permanent peripheral nerve disorder which may take place separately or more often as part of more complex pathologies.

A pathological classification of peripheral neuropathies was suggested by P. K. Thomas-International Conference on Peripheral Neuropathies, 24th–25th June 1981, Madrid p. 79, Excerpta Medica, as reported in Table I.

TABLE I

| Pathological Classification of Peripheral Neuropathies |
|---|
| 1. Disorders generally leading to axon loss |
|    a. Neurophaties |
|       Spinal muscolar atrophy |
|       Degeneration of dorsal root cells and autonomous ganglion cells |
|    b. Axonopathies |
|       Proximal axonopathy |
|       Distal axonopathy |
|       Focal axonal interruption |
| 2. Disorders essentially concerning supporting tissues |
|    Disorders of Schwann cells |
|    Myelinopathies |
|    Disorders of the neural connective tissue |
|    Vascular disturbances |

A general separation may be made between disorders which essentially produce axon loss in peripheral nerves and those in which the nervous fibre lesion is secondary to disturbances concerning the supporting structures, including Schwann cells and myelin, connective nervous tissues and the vascular system.

The first category of disturbances may be further subdivided between conditions in which complete loss of the neuron takes place (neuropathies) and the ones in which a selective axone destruction takes place.

The same author suggests a peripheral neuropathy classification on etiologic basis, as reported in Table II.

TABLE II

| Etiologic Classification of Peripheral Neuropathies |
|---|
| Neuropathies due to: |
|    Physical agents |
|    associated to systemic diseases |
|    toxic neuropathies |
|    nutritional deficiencies |
|    inflammations and postinfection disorders |
|    neuroplasias and paraproteinemia |
|    hereditary factors |
|    cryptogenic factors |

Purpose of the present invention is to provide pharmaceutical compositions possessing a proved activity as reproductive agent of the nerve fibers and effectiveness in the therapy of human diseases associated with neuronal damages, particularly in the therapy of peripheral neuropathies, of cerebrovascular diseases, of traumas at the cerebral level and of chronic neurodegenerative diseases, the pharmaceutical compositions being devoid of toxicity or side effects.

This results is obtained using derivatives of phosphatidyl carnitine or their pharmacologically acceptable salts of formula (I):

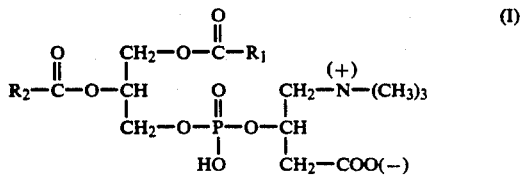

in their racemic or optically active form, wherein $R_1$ and $R_2$, equal or different, are radicals of aliphatic acids of from 1 to 20 C atoms, with linear or branched chains, saturated or mono- or polyunsaturated, preferably radicals of pivalic-, lauric-, myristic-, palmitic-, palmitoleic-, stearic-, oleic-, linoleic-, linolenic- or, arachidonic-acid for the preparation of pharmaceutical compositions active as reproductive agents of the nerve fibers in the therapy of human diseases associated with neuronal damages.

Results obtained in the last ten years show that nerve cells, both in vitro and in vivo, are apt to undergo morphological and functional changes in answer to intrinsic or extrinsic changes in their micro-environment. This ability, resumed in the term neuroplasticity, was shown to be necessary for the manifestation of reparative processes following neuronal damages. The use of neuronal cultures is very useful to evaluate the efficacy of the new active principles in facilitating the neuroplasticity processes and thus in improving the neurological results following neuronal damages in humans.

The use of neuronal cultures is basic for such evaluations, as the induction of morphologic changes (e.g. the neuritic growth) and/or functional changes of such cells is ruled by processes implied in neuroplasticity.

Therefore, agents which are able to induce or facilitate the neuritic growth in vitro are the ones apt to facilitate the manifestation of neuroplastic phenomena.

In order to demonstrate the activity of the phosphatidyl-carnitine derivatives according to the present invention, we performed numerous tests in vitro.

An example is reported here, for illustrative purposes.

TEST 1

This test was made to prove the biological activity of dipalmitoyl phosphatidyl carnitine on mice neuroblastoma cells of type C 1300 (Neuro-2a (N2A) clone obtained from the American Cell Type Culture Collection, Betheshda, Md.). As comparison acetyl-L-carnitine was selected, as its activity in the therapy of peripheral neuropathies was described e.g. in the Italian patent 1.196.564 filed Aug. 4, 1986.

The neuroblastoma neuronal cultures may show in suitable conditions various functions characteristic of mature neurons, allowing furthermore qualitative and quantitative analyses of biochemical parameters which can be correlated to various development stages, as described in Denis-Donini D.; Augusti Tocco G.; (1980) Molecular and Lecitin Probe Analyses of neuronal Differentiations; in Moscona, Monroy, Neuronal Development in Model Systems, p. 323–348, Academic Press, N.Y.

MATERIALS AND METHODS a) Solutions Employed

Dipalmitoyl phosphatidyl carnitine was dissolved at a concentration of 10 mg/ml TRIS/HCl 50 nM pH 7.8, sonicated for different times (CD 1,2: 3 min; CD 3,4: 2 min; CD 5,6: 1 min:), filtered on Acrodisc Filter 45 μm (Gelman) and diluted to a final concentration of $1 \times 10^{-4}$M with culture medium containing Dulbecco's modified Eagle medium (Dmem, Flow), 10% of fetal bovine serum (FCS, lot 2 AO2 Seromed), penicillin (100 units/ml, Irvine) and L-glutamine (2 mM, Sigma).

Acetyl-L-carnitine was dissolved directly in the described culture medium, filtered and then diluted with the medium to obtain final concentrations:

$1 \times 10^{-2}$M, $5 \times 10^{-3}$M, $1 \times 10^{-3}$M, $5 \times 10^{-4}$M, $1 \times 10^{-4}$M, $5 \times 10^{-5}$M.

b) Cultures Employed, Incubation Method, Analytical Methods:

N2A cells were plated at a density of 10,000 cells/well (24-costar) in the above described culture medium. After 24 hrs on the plate, the culture medium was substituted with 350 μm fresh culture medium with and without the phosphatidyl carnitine derivatives and left for 24 hrs for the morphological evaluation, and 48 hrs for the dosage of the incorporation of methyl$^3$-H thymidine ($^3$HTdr, Amersham) in DNA, as described by Leon A., Facci L., Benvegnù D., Toffano G., in Morphological and Biochemical Effect of Ganglioside in neuroblastoma cells, Dev. Neurosci. 5: 108–114, (1982), and for the count of vital cells by colorimetry-MTT (3-(4,5-dimethylazol-2-yl)-2,5-diphenyltetrazolium) as described by Mosmann T. in "Rapid Colorimetric Assay for Cellular Growth and Survival: Application to Proliferation Cytotoxicity Assay. J. Immun. Methods 65, 55–63 (1983).

RESULTS

Figure 1B:
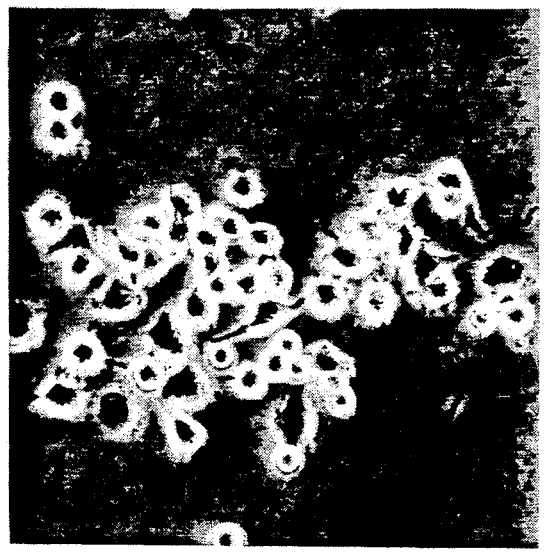
Figure 1D:
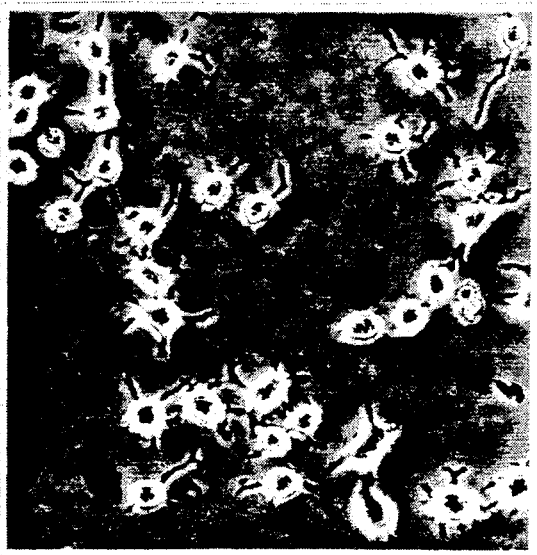

Dipalmitoyl phosphatidyl carnitine was found active in inducing morphological differentiation in neuroblastoma cells N2A as evident from FIG. 1d; on the contrary, acetyl-L-carnitine, at the different concentrations employed, was completely inactive, as evident from FIG. 1b, not having induced any modification with respect to the control (FIG. 1a).

Table III reports the results obtained for the group of control cells, for the treatment with acetyl-L-carnitine and for the one with dipalmitoyl phosphatidyl carnitine in racemic form, respectively in relation to the percentage of cells with neurites, to the incorporation of methyl$^3$-H thymidine, to the count of vital cells by colorimetry and to the ratio between the last two data.

TABLE III

| concent. | % cells with neurites | $^3$HTdr dpm/2h/well | MTT D.O. = 570–630 | $^3$HTdr/ MTT |
|---|---|---|---|---|
| | | Control | | |
| | 5 | 55271 ± 2540 | 0.353 ± 0.011 | 157 × 10$^3$ |
| | | Acetyl-L-carnitine | | |
| $1 \times 10^{-2}$M | 5 | 51374 ± 5001 | 0.313 ± 0.010 | 165 × 10$^3$ |
| $5 \times 10^{-3}$M | 5 | 49637 ± 1153 | 0.286 ± 0.015 | 173 × 10$^3$ |
| $1 \times 10^{-3}$M | 5 | 49835 ± 4076 | 0.347 ± 0.012 | 144 × 10$^3$ |
| $5 \times 10^{-4}$M | 5 | 53634 ± 1825 | 0.334 ± 0.010 | 161 × 10$^3$ |
| $1 \times 10^{-4}$M | 5 | 51014 ± 2125 | 0.336 ± 0.010 | 152 × 10$^3$ |
| $1 \times 10^{-5}$M | 5 | 46255 ± 6047 | 0.361 ± 0.008 | 128 × 10$^3$ |
| | D,L-dipalmitoyl-phosphatidylcarnitine | | | |
| $1 \times 10^{-4}$M | 37 | 31595 ± 306 | 0.223 ± 0.011 | 142 × 10$^3$ |

From the data reported on Table III one can see that dipalmitoylphosphatidyl carnitine proved to be active in increasing the number of cells with neurites, in decreasing the incorporation of $^3$-HTdr in DNA (an index of lower proliferation and therefore of higher cellular differentiation), while acetyl-L-carnitine proved to be inactive.

One should observe also that the results obtained by colorimetric dosage with MTT put in evidence the total absence of a toxic effect on the part of the tested compounds.

The pharmaceutical compositions obtained employing the phosphatidyl-carnitine derivatives or their pharmacologically acceptable salts according to the present invention contain a quantity of active principle comprised between 100 and 1000 mg, preferably between 200 and 500 mg, and may be prepared in a form suitable for administration per os or parenteral according to the formulations normally employed in pharmaceutical technique.

The therapeutic method for the therapy of human pathologies due to neuronal damages, characterised by the administration of a therapeutically effective amount of phosphatidyl carnitine derivatives, or of their pharmacologically acceptable salts of general formula (I) is effected by the administration, per os or parenteral, of an amount of active principle comprised between 10 and 80 mg/kg/day, preferably between 20 and 50 mg/kg/day in from 2 to 4 administrations per day.

For illustrative and not limitative purposes, we report some examples of practical realization of the pharmaceutical preparations according to the present invention.

INJECTABLE PHARMACEUTICAL COMPOSITIONS

EXAMPLE 1

A 2 ml vial contains:

| | |
|---|---|
| dipalmitoyl-phosphatidyl-L-carnitine | mg 200 |
| monobasic sodium phosphate | mg 2.4 |
| bibasic sodium phosphate | mg 2.26 |
| bidistilled apyrogenic water as needed to | ml 2 |

EXAMPLE 2

A 2 ml vial contains:

| | |
|---|---|
| dipivaloyl-phosphatidyl-L-carnitine | mg 200 |
| monobasic sodium phosphate | mg 2.4 |
| bibasic sodium phosphate | mg 2.26 |
| bidistilled apyrogenic water as needed to | ml 2 |

EXAMPLE 3

A 2 ml vial contains:

| | |
|---|---|
| dimyristoyl-phosphatidyl-L-carnitine | mg 200 |
| monobasic sodium phosphate | mg 2.4 |
| bibasic sodium phosphate | mg 2.26 |
| bidistilled apyrogenic water as needed to | ml 2 |

EXAMPLE 4

A 3 ml vial contains:

| | |
|---|---|
| dipalmitoyl-phosphatidyl-L-carnitine | mg 300 |
| monobasic sodium phosphate | mg 3.21 |
| bibasic sodium phosphate | mg 3.39 |
| mannitol | mg 30 |
| bidistilled apyrogenic water as needed to | ml 3 |

EXAMPLE 5

A 3 ml vial contains:

| | |
|---|---|
| dipivaloyl-phosphatidyl-L-carnitine | mg 300 |
| monobasic sodium phosphate | mg 3.21 |
| bibasic sodium phosphate | mg 3.39 |
| mannitol | mg 30 |
| bidistilled apyrogenic water as needed to | ml 3 |

EXAMPLE 6

A 3 ml vial contains:

| | |
|---|---|
| dimyristoyl-phosphatidyl-L-carnitine | mg 300 |
| monobasic sodium phosphate | mg 3.21 |
| bibasic sodium phosphate | mg 3.39 |
| mannitol | mg 30 |
| bidistilled apyrogenic water as needed to | ml 3 |

ORAL PHARMACEUTICAL COMPOSITIONS

EXAMPLE 7

A gelatine capsule contains:

| | |
|---|---|
| dipalmitoyl-phosphatidyl-L-carnitine | mg 400 |
| vegetable oil | mg 270 |
| bee wax | mg 1 |

EXAMPLE 8

A gelatine capsule contains:

| | |
|---|---|
| dipivaloyl-phosphatidyl-L-carnitine | mg 400 |
| vegetable oil | mg 270 |
| bee wax | mg 1 |

EXAMPLE 9

A gelatine capsule contains:

| | |
|---|---|
| dimyristoyl-phosphatidyl-L-carnitine | mg 400 |
| vegetable oil | mg 270 |
| bee wax | mg 1 |

EXAMPLE 10

A gelatine capsule contains:

| | |
|---|---|
| dipalmitoyl-phosphatidyl-L-carnitine | mg 500 |
| vegetable oil | mg 270 |
| bee wax | mg 1 |

EXAMPLE 11

A gelatine capsule contains:

| | |
|---|---|
| dipivaloyl-phosphatidyl-L-carnitine | mg 500 |
| vegetable oil | mg 270 |
| bee wax | mg 1 |

EXAMPLE 12

A gelatine capsule contains:

| | |
|---|---|
| dimyristoyl-phosphatidyl-L-carnitine | mg 500 |
| vegetable oil | mg 270 |
| bee wax | mg 1 |

EXAMPLE 13

A dragee contains:

EXAMPLE 14

A dragee contains:

| | |
|---|---|
| dipalmitoyl-phosphatidyl-L-carnitine | mg 250 |
| mannitol | mg 100 |
| microcrystalline cellulose | mg 25 |
| starch | mg 5 |
| sucrose | mg 30 |
| lacquer | mg 5 |

EXAMPLE 14

A dragee contains:

| | |
|---|---|
| dipivaloyl-phosphatidyl-L-carnitine | mg 250 |
| mannitol | mg 100 |
| microcrystalline cellulose | mg 25 |
| starch | mg 5 |
| sucrose | mg 30 |
| lacquer | mg 5 |

EXAMPLE 15

A dragee contains:

| | |
|---|---|
| dimyristoyl-phosphatidyl-L-carnitine | mg 250 |
| mannitol | mg 100 |
| microcrystalline cellulose | mg 25 |
| starch | mg 5 |
| sucrose | mg 30 |
| lacquer | mg 5 |

EXAMPLE 16

A cachet contains:

| | |
|---|---|
| dipalmitoyl-phosphatidyl-L-carnitine | mg 450 |
| mannitol | mg 100 |
| lactose | mg 100 |

EXAMPLE 17

A cachet contains:

| | |
|---|---|
| dipivaloyl-phosphatidyl-L-carnitine | mg 450 |
| mannitol | mg 100 |
| lactose | mg 100 |

EXAMPLE 18

A cachet contains:

| | |
|---|---|
| dimyristoyl-phosphatidyl-L-carnitine | mg 450 |
| mannitol | mg 100 |
| lactose | mg 100 |

We claim:

1. A pharmaceutical composition comprising a therapeutically effective amount of at least one compound having the formula (I)

$$\begin{array}{c} \text{R}_2-\overset{O}{\underset{\parallel}{C}}-O-\overset{CH_2-O-\overset{O}{\underset{\parallel}{C}}-R_1}{\underset{CH_2-O-\overset{O}{\underset{\parallel}{P}}-O-CH}{CH}} \overset{CH_2-\overset{(+)}{N}-(CH_3)_3}{\underset{CH_2-COO(-)}{}} \\ \text{HO} \end{array} \quad (I)$$

in racemic or optically active form, wherein $R_1$ and $R_2$, are the same or different, and are $C_1$-$C_{20}$, linear or branched, saturated, or mono- or poly-unsaturated aliphatic acids or a pharmacologically acceptable salt thereof; and a pharmaceutically acceptable carrier.

2. The pharmaceutical composition according to claim 1, wherein $R_1$ and $R_2$ each are radicals selected from the group consisting of pivalic, lauric, myristic, palmitic, palmitoleic, stearic, oleic, linoleic, linolenic and arachidonic acid.

3. The pharmaceutical composition according to claim 1, wherein said human pathologies associated with neuronal damages are selected from the group consisting of peripheral neuropathies, cerebrovascular diseases, traumas at cerebral level and chronic neurodegenerative diseases.

4. The pharmaceutical composition according to claim 1, wherein said compound is present in an amount of between 100 and 1000 mg.

5. The pharmaceutical composition according to claim 4, wherein said compound is present in an amount of between 200 and 500 mg.

6. A method for treating human pathologies due to neuronal damages, which comprises administrating to a patient in need thereof a therapeutically effective amount of a compound having the formula (I)

$$\begin{array}{c} \text{R}_2-\overset{O}{\underset{\parallel}{C}}-O-\overset{CH_2-O-\overset{O}{\underset{\parallel}{C}}-R_1}{\underset{CH_2-O-\overset{O}{\underset{\parallel}{P}}-O-CH}{CH}} \overset{CH_2-\overset{(+)}{N}-(CH_3)_3}{\underset{CH_2-COO(-)}{}} \\ \text{HO} \end{array} \quad (I)$$

wherein $R_1$ and $R_2$, are the same or different, and are $C_1$-$C_{20}$ linear or branched chain, saturated or mono- or poly-unsaturated aliphatic acids, or a pharmacologically acceptable salt thereof.

7. The method according to claim 6, wherein $R_1$ and $R_2$ each are radicals selected from the group consisting of pivalic, lauric, myristic, palmitic, palmitoleic, stearic, oleic, linoleic, linolenic and arachidonic acid.

8. The method according to claim 6, wherein said human pathologies are selected from the group consisting of peripheral neuropathies, cardiovascular diseases, traumas at the cerebral level and chronic neurodegenerative diseases.

9. The therapeutic method of claim 6, wherein said therapeutically effective amount is approximately 100 mg to approximately 1000 mg.

10. The therapeutic method of claim 9, wherein said therapeutically effective amount is approximately 200 to approximately 500 mg.

* * * * *